United States Patent [19]
Steinman

[11] Patent Number: 5,849,497
[45] Date of Patent: Dec. 15, 1998

[54] SPECIFIC INHIBITION OF THE POLYMERASE CHAIN REACTION USING A NON-EXTENDABLE OLIGONUCLEOTIDE BLOCKER

[75] Inventor: Charles Steinman, Setauket, N.Y.

[73] Assignee: The Research Foundation of State University of New York, Stony Brook, N.Y.

[21] Appl. No.: 832,449

[22] Filed: Apr. 3, 1997

[51] Int. Cl.$^6$ .............. C12Q 1/68; C12P 19/34; C07H 21/04
[52] U.S. Cl. ............ 435/6; 435/91.3; 536/24.33
[58] Field of Search ............ 435/6, 91.3; 436/94; 536/24.32, 24.33; 935/17, 77

[56] References Cited

U.S. PATENT DOCUMENTS

| | | | |
|---|---|---|---|
| 5,348,853 | 9/1994 | Wang et al. | 4354/6 |
| 5,391,480 | 2/1995 | Davis et al. | 435/6 |
| 5,466,591 | 11/1995 | Abramson et al. | 435/194 |
| 5,487,985 | 1/1996 | McClelland et al. | 435/91.2 |
| 5,534,424 | 7/1996 | Uhlen et al. | 435/91.2 |

OTHER PUBLICATIONS

Greisne et al. PCR primers and probes for the 16S rRNA gene of most species of pathogenic bacteria, including bacteria found in cerebrosinal fluid. J. Clin. Microbiol. 32(2): 335–351, Feb. 1994.

Perkin Elmer. PCR Systems, Reagents and Consumables 1995–1996 (Catalog), pp. 15–18.

Beaton et al. "Synthesis of oligonucleotide phosphorodithioates" in Oligonuclelotide and Analogues, Eckstein, ed. IRL Press, New York. pp. 109–135, 1991.

Ramsay et al. "Oligonucleoside Boranophosphate" in Protocols for Oligonucleotides Analogs, Agrawal, ed. Humana Press, Totowa, New Jersey. pp. 225–243, 1993.

Uhlmann et al. "Antisense oligonucleotides: A new therapeutic principle," Chem. Rev. 90(4): 543–584, Jun. 1990.

Single base pair mutation analysis by PNA directed PCR clamping; H. Orum, P. E. Nielsen, M. Egholm, R. H. Berg, O. Buchardt & C. Stanley; Nucleic Acids Research, 1993, vol. 21, No. 23; pgs. 5332–5336.

A novel blocker–PCR method for detection of rare mutant alleles in the presence of an excess amount of normal DNA; T. Seyama, T. Ito, T. Hayashi, T. Mizuno, N. Nakamura & M. Akiyama; Nucleic Acids Research, vol. 20, No. 10; pp. 2493–2496.

Mutation Detection in Leber's Hereditary Optic Neuropathy By PCR With Alle–Specific Priming; Biochemical and Biophysical Research Communications; vol. 175, No. 2; 1991; pp. 631–636.

*Primary Examiner*—George C. Elliott
*Assistant Examiner*—Thomas G. Larson
*Attorney, Agent, or Firm*—Proskauer Rose LLP

[57] ABSTRACT

A process is disclosed for inhibiting the amplification of a DNA template by subjecting a sample of biological material containing nucleic acid to the polymerase chain reaction (PCR) using a DNA polymerase deficient in 5' exonuclease activity. The method comprises forming a PCR admixture comprising the DNA template, first and second oligonucleotide primers which are complementary to separated regions of the nucleic acid template, a non-extendable oligonucleotide blocker which is complementary to the inter-primer region of the DNA, and the DNA polymerase lacking 5' exonuclease activity, and subjecting the PCR admixture to at least one PCR thermocycle. The DNA polymerase lacking 5' exonuclease activity is incapable of excising the non-extendable blocker which anneals to the DNA template during the PCR, thereby inhibiting amplification which would otherwise occur during the PCR. Preferably, the DNA polymerase lacking 5' exonuclease activity is the Stoffel fragment of Taq polymerase. The method may be adapted for detecting whether DNA from specific pathogens is present in a sample material.

22 Claims, 5 Drawing Sheets

SPECIFIC INHIBITION OF THE POLYMERASE CHAIN REACTION USING A NON-EXTENDABLE OLIGONUCLEOTIDE BLOCKER

REFERENCE TO GRANTS

The work associated with this application was supported in part by grants AR33278 and AR39939 from the National Institute of Health.

FIELD OF THE INVENTION

This invention relates to a method for selectively inhibiting the amplification of DNA sequences using the polymerase chain reaction (PCR). More particularly, this invention relates to a novel method for inhibiting amplification of a nucleic acid template by binding a non-extendable oligonucleotide blocker to the inter-primer region of a nucleic acid template.

This technique has both clinical and research applications.

BACKGROUND OF THE INVENTION

DNA analysis is currently used in many research, diagnostic and forensic procedures. Some research strategies currently used include the polymerase chain reaction with broad range primers for amplifying bacterial targets, representational difference analysis and genotype determination.

For many reasons, it is important to be able to identify the genus, species or other taxonomic classification to which a bacterium belongs, or to be able to rapidly and accurately identify a tissue genotype. For example, such classification is important in order to distinguish different disease causing pathogens, such as in septic arthritis. It is imperative that taxonomic identification be expedient for pathogenic organisms, such as viruses, bacteria, protozoa, and multicellular parasites. This will assist in diagnosis and treatment of human and animal diseases, as well as studies in epidemiology and ecology.

Traditionally the identification of bacterial species, viruses, protozoa, and multicellular parasites has been achieved by studying the morphology, growth requirements, fermentation patterns, and antibiotic sensitivity of the pathogenic organisms as well as by immunologic methods. These methods are time consuming and require highly trained personnel. Moreover, the presence of some organisms cannot be recognized by these methods. More recently, methods have been developed for identification of pathogenic organisms by detection of RNA and DNA sequences using the polymerase chain reaction (PCR).

The recent development of the PCR has provided an important tool for the detection of nucleic acid sequences at low concentrations. The method allows amplification of a selected target region of DNA by providing two DNA primers. Each primer is complementary to a base sequence on one of the two complementary DNA strands, located at the ends of the target region. Each primer can hybridize to its complementary site after the DNA strands are separated. The 5' ends of the single-stranded primers are then extended using DNA polymerase to form double-stranded molecules that reach at least as far as the region complementary to the other primer. The double-stranded molecules are then separated by heat denaturation again, and the process is repeated.

Repetition of this process a number of times results in the exponential generation of multiple copies of DNA that correspond in sequence to the target region. Accordingly, a small number of target sequences can be exponentially amplified and the resulting large number of molecules then reliably detected.

Some recent applications of the PCR have employed primers that are complementary to more than one DNA target and that therefore can amplify multiple such sequences differing mainly in the sequences between those complementary to the primers, called here the inter-primer region. One such application takes advantage of the fact that some DNA sequences in the bacterial genes that code for ribosomal RNA's are phylogenetically conserved among different species. The degree of conservation varies with the location within these genes. Thus some such sequences are common to groups of phylogenetically related species. The sizes of those phylogenetic groups can vary greatly and can include, for example, only very closely related species or, at the other extreme, can include all species of bacteria. One can therefore use one primer pair to amplify DNA from any member of such a related group of bacterial species whose presence might be suspected in a clinical specimen. The identity of the species actually amplified can then be narrowed down further.

The latter can be accomplished by several methods including use of additional PCR's with primers that target smaller subgroups of bacteria, Southern blotting and analysis of restriction fragment sites. Many of these methods are technically difficult, expensive and time consuming. An alternative method of narrowing down the identity of such an amplified bacterial DNA would be by use of the present invention to specifically block amplification of selected members of the group of DNA's that can be amplified by that pair of primers.

Another possible application of the present invention is in use of the PCR for genotyping where two allotypes are both amplified by the same primers and differ by an insertion that is too short to allow their amplicons to be easily distinguished by size alone. Amplification of the allotype possessing the insert could be blocked specifically, allowing them to be distinguished. Still another possible use for the present invention is in representational difference analysis (RDA) where amplification of selected sequences could be blocked, for example, at the stage of preparing a genomic representation.

Such sequence-dependent blocking can be achieved by using a method developed by Henrik Orum et al. which utilizes peptide nucleic acids (PNA) which bind to specific regions on a DNA template to form a PNA/DNA complex. The PNA/DNA complex formed is more stable than a DNA/DNA complex and PNA cannot act as a primer. A specific PNA complementary to an inter-primer region on a nucleic acid sequence is synthesized and allowed to hybridize to the specific DNA inter-primer region during PCR amplification. Once the PNA/DNA complex is formed, amplification is blocked since the PNA is unable to be extended or removed.

This process is limited in that PNA are not easily synthesized and therefore are not readily available. Moreover, the per base cost is much more expensive than a corresponding DNA oligonucleotide blocker. Therefore this method is not economically efficient or widely available.

The present invention describes an alternative method by which an easily synthesized oligonucleotide blocker that binds specifically to a sequence in the inter-primer region can block the amplification of that target by preventing extension of one of the primers. To accomplish this, the blocking oligonucleotide is made non-extendable and therefore cannot itself act as primer which might result in competitive nonspecific inhibition of amplification of other PCR products. Also, it must not be removed during amplification, as would normally result from the 5' exonuclease activity present in Taq polymerase, an enzyme that is normally used for the PCR. To keep that from occurring, we substitute the Stoffel fragment of Taq polymerase, a form of Taq polymerase that has been altered to eliminate that exonuclease activity.

The possible uses of the present invention, described above, are presented as only a few possible examples of how the present invention can be used in scientific research. This discussion is not meant to limit the present invention in any way.

SUMMARY OF THE INVENTION

In its most general form, the present invention comprises a method for inhibiting amplification of a specific nucleic acid target sequence in a DNA which is being subjected to PCR. The method comprises forming a PCR admixture comprising the DNA sequence, first and second oligonucleotide primers which are complementary to first and second separated regions on the DNA template, a non-extendable oligonucleotide blocker which is complementary to at least a portion of an inter-primer region located between the first and second primer regions on the nucleic acid template, and a DNA polymerase which lacks 5' exonuclease activity, as well as the usual PCR buffers and deoxynucleotide triphosphate precursors. This PCR admixture is then subjected to at least one PCR thermocycle comprising hybridization, primer extension, and denaturation. During the PCR thermocycle, the non-extendable blocker anneals to the inter-primer region on the nucleic acid template and prevents complete extension of the first oligonucleotide primer in the 5' to 3' direction. Furthermore, since the DNA polymerase lacks 5' exonuclease activity, the non-extendable blocker cannot be digested and amplification of the nucleic acid sequence is prevented.

Amplification of the DNA target sequence is inhibited only when the non-extendable oligonucleotide blocker can bind to a complementary sequence located within its inter-primer region. The inventive process may therefore be described as a process for sequence-specific inhibition of PCR-based amplification.

In a preferred embodiment, the nucleic acid polymerase employed in the practice of this invention is the Stoffel fragment of Taq polymerase. This fragment lacks 5' exonuclease activity, a necessary condition for carrying out the present invention.

As used herein, the term "primer" refers to an oligonucleotide, whether occurring naturally as in a purified restriction digest or produced synthetically, which is capable of acting as a point of initiation of synthesis when placed under conditions in which a primer extension product complementary to a target sequence is induced. The primers used in the present invention are substantially complementary to separated regions on the nucleic acid template.

For the purpose of this application, the terms "first primer region" and "second primer region" refer to the regions on the nucleic acid sequence that are complementary to the first and second primers. It is also noted, that for the purpose of this application, the primers are designated "first" and "second" only to indicate to which primer regions they will bind.

The term "non-extendable oligonucleotide blocker" refers to an oligonucleotide that is made non-extendable by adding bases to the 3' end that are not complementary to the target sequence and therefore do not base-pair and cannot be enzymatically extended. Other methods of making the oligonucleotide non-extendable can be used. The blocker used in the present invention binds to the "inter-primer" region which is a region on the DNA template located between the two primer regions.

The "Stoffel fragment of Taq polymerase" is a known and commercially available DNA polymerase capable of adding nucleotides to the extending end of a primer, but lacking 5' exonuclease activity. As a result, once the non-extendable oligonucleotide blocker anneals to its complementary region on a DNA template, it cannot be removed. On the other hand, if the intact Taq polymerase (which possesses 5' exonuclease activity) is used instead of the Stoffel fragment, the blocker will be removed, and amplification will not be substantially inhibited during PCR, thereby defeating the purpose of the present invention.

A "PCR thermocycle" is the sequence of temperature changes during which the PCR takes place. It typically involves the cycling of temperatures from a first temperature to a second temperature, then to a third temperature and then back to the first temperature generally pausing at each of these temperatures for a period of time. Each step of the PCR, namely, hybridization, primer extension, and denaturation, takes place predominantly at one of these temperatures. Sometimes only two temperatures are used instead of three, with the annealing and primer extension taking place at the same temperature. The temperatures used are derived empirically but are largely defined by the melting points of the oligonucleotides and the target sequences involved. It is noted that, the present invention is not limited to PCR thermocycling technology, since other analogous primer-dependent polymerase extension methods may be devised to detect specific sequences that are not dependent on temperature change and where the present method might still work to inhibit such amplifications substantially as described here.

When the PCR using the Stoffel fragment of Taq polymerase is performed on a PCR admixture which includes a sequence in the inter-primer region that is complementary to the blocker, the blocker will anneal to that sequence. The annealing of the blocker within the inter-primer region prevents the first primer from extending to the region of second primer. Thus, the specific DNA sequence will not be amplified.

The present invention of sequence specific inhibition of PCR-based amplification can be adapted to determine whether a biological material contains a particular target DNA sequence (or group of sequences) that is among those that are potentially amplifiable by a specific pair of primers that are capable of amplifying multiple targets differing from one another in their inter-primer sequences. In this aspect of the invention, the biological material containing DNA is mixed with a PCR admixture comprising primers which are complementary to portions of that DNA, (which defines the target region), DNA polymerase lacking 5' exonuclease activity, and the non-extendable blocker. The PCR admixture is subjected to at least one round of amplification. Thereafter, conventional methods are used to determine if amplification has occurred. If the biological material contains the particular target DNA sequence whose inter-primer region contains a sequence complementary to that of the blocker (not including its 3'-tail), the non-extendable blocker will bind to its complementary sequence in the inter-primer region, and prevent the extension of the primers, thus blocking amplification. On the other hand, if the biological material contains a different target DNA sequence, one that lacks such a complementary sequence in its inter-primer region, the non-extendable blocker would not be able to bind and therefore the primers will be extended and amplification will occur.

Conventional means, such as electrophoresis and ethidium bromide staining, may be used to detect the presence or absence of the amplified target DNA. When inhibition occurs, the biological material in the PCR admixture is identified as a nucleic acid sequence having the specific inter-primer region. This would be considered a positive result when compared to a control that was not blocked. If amplification occurs, then this would be a negative result and would indicate that the biological material having the specific inter-primer region is not the one amplified.

Thus, the present invention provides a novel method for identifying biological material, such as bacteria and viruses by inhibiting the amplification of specific targets when subjected to PCR technology.

In a preferred embodiment of the invention, the binding of the non-extendable oligonucleotide blocker is favored over the binding of the primers. This is achieved by using a non-extendable oligonucleotide blocker designed to have a higher melting point than the melting points possessed by the primers. This non-extendable oligonucleotide blocker can be manufactured by making the blocker significantly longer than the primers. The higher melting point gives the blocker a kinetic advantage at certain temperatures over that of its associated primers and assures its presence as a stable duplex when encountered by the extending primers.

To further assure the binding of the blocker, an additional high temperature incubation period is used in the amplification process. This high temperature incubation will be too high to allow any primer/nucleic acid duplex to be formed, thereby assuring that the higher-temperature-annealing non-extendable oligonucleotide blocker starts to anneal before temperature is further lowered to allow the primers to anneal. It is possible that under some circumstances, it may be unnecessary for the blocker to have such a kinetic advantage over the primer in binding in order to inhibit its extension significantly. It should be noted that the Stoffel fragment of Taq polymerase is a heat-stable enzyme capable of withstanding the high temperatures associated with the PCR thermocycles.

In another aspect of the invention, a kit for determining the presence of one or more particular target DNA sequences among multiple such sequences that are potentially amplifiable by one or more primer pairs is described. The kit contains the necessary reagents for identifying those particular target DNA sequences, including primers, non-extendable oligonucleotide blockers, PCR buffers, as well as directions giving a protocol for carrying out the procedure. The present invention strategically uses oligonucleotides (including primers and blockers) that are designed to minimize interactions among themselves so as to eliminate low molecular weight artifacts that might inhibit amplification non-specifically. For this reason, for example, oligonucleotides having 3' termini that could base-pair and form an extendable end either with itself or with another oligonucleotide present in the same reaction are avoided. In addition, both external and internal controls are typically used for comparison purposes to further eliminate the effects of nonspecific inhibition.

One specific application of the present invention is to distinguish among bacterial ribosomal sequences from different species of bacteria which are all primed by the same broad range primers.

Another application is to prevent unwanted amplification of a specific sequence. For example, such a sequence might be present as a contaminating bacterial DNA whose amplification would obscure the presence of other bacterial DNA's whose presence is being queried, as in conjunction with primers targeting multiple bacterial ribosomal targets as described above. Such a known contaminating DNA is present in many preparations of Taq DNA polymerase, for example, and might obscure the presence of small amounts of other bacterial DNA's in a biological specimen using broad range primers.

This technique can also be used for genotyping by blocking amplification of one allotype differing from another allotype by only a short insertion to which a blocker could be directed. The allotype lacking that insertion would then be detectible in the presence of the other allotype if both were amplifiable by the same pair of primers.

The present invention can also be used in representational difference analysis (RDA). Similar to the procedure described above, the admixture of the present invention can be made to include non-extendable oligonucleotide blockers complimentary to the inter-primer region of specific sequences that might not be desired in the representation. An example might be a highly repetitive sequence that might prove difficult to efficiently subtract. Once the non-extendable oligonucleotide blocker binds in the inter-primer region of such sequences, it will inhibit their extension and amplification and thus exclude them from the representation.

DETAILED DESCRIPTION OF THE INVENTION

In accordance with the present invention, a method of inhibiting amplification of a nucleic acid template located on a nucleic acid sequence comprises the forming of a PCR admixture and subjecting the PCR admixture to at least one PCR thermocycle.

The PCR admixture is comprised of the following: a nucleic acid sequence having a nucleic acid template with first and second primer regions and an inter-primer region thereon, first and second oligonucleotide primers which are complementary to first and second primer regions, a non-extendable oligonucleotide blocker, and a polymerase lacking 5' exonuclease activity. The manner in which the inventive method inhibits amplification during a PCR thermocycle will now be described by reference to the accompanying drawings.

Figure 1:
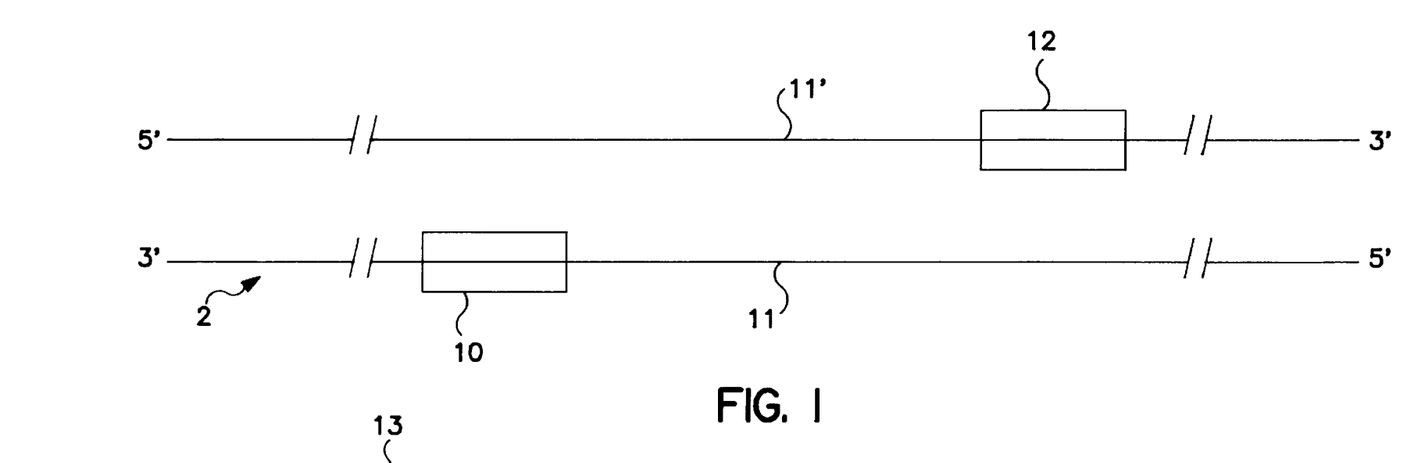
FIG. 1 schematically shows the spacial arrangement of a first primer region, a second primer region on a DNA template.
Figure 2:
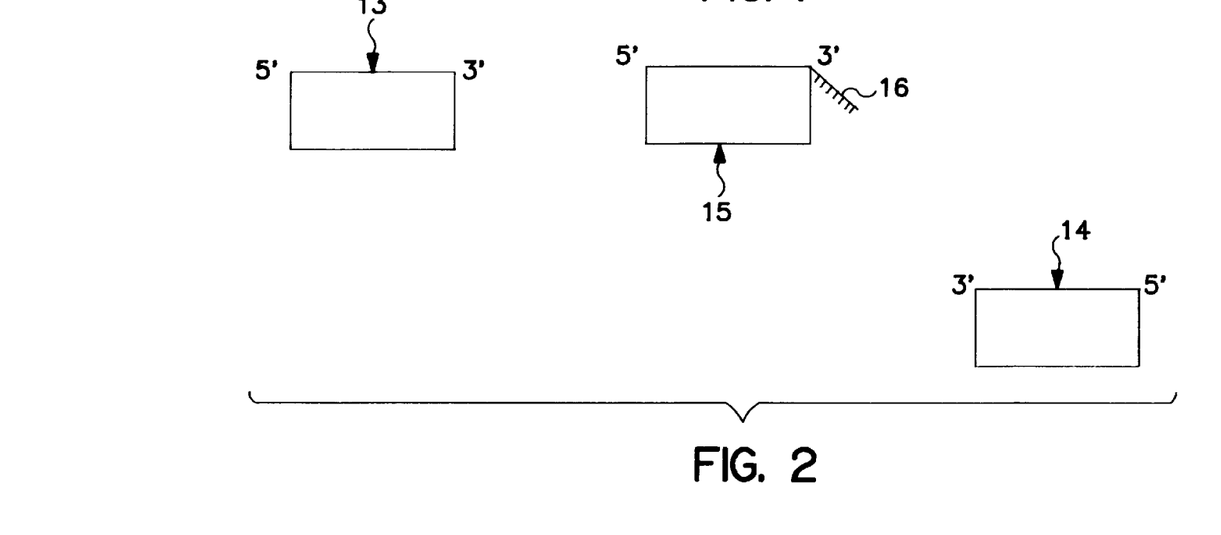
FIG. 2 schematically shows a first oligonucleotide primer, a second oligonucleotide primer and a non-extendable oligonucleotide blocker.

FIG. 1 schematically shows a double stranded DNA template (2) on a DNA sequence. The DNA template has a first primer region (10), a second primer region (12), an inter-primer region (11). FIG. 2 schematically shows a first oligonucleotide primer (13), a second oligonucleotide primer (14), and a non-extendable oligonucleotide blocker (15). The non-extendable oligonucleotide blocker (15) has a 3' tail (16) consisting of at least one mismatch.

The first primer (13) is complementary to the first primer region (10) of DNA template (2), and the second primer (14) is complementary to the second primer region (12). Between the first primer region (10) and the region complementary to the second primer region (12) is the inter-primer region (11) which contains a sequence that is substantially complementary to the non-extendable oligonucleotide blocker (15).

One way to make the non-extendable oligonucleotide blocker (15) non-extendable is by adding at least one non-complementary base to the 3' end (16) (the tail). In practice more than one such non-complementary base is added to the tail since a single base may not suffice to prevent extension and, in addition, may be unintentionally removed by enyzamatic activity that might be present in the reaction mixture. Other methods can be used to make the blocker non-extendable.

Figure 3:
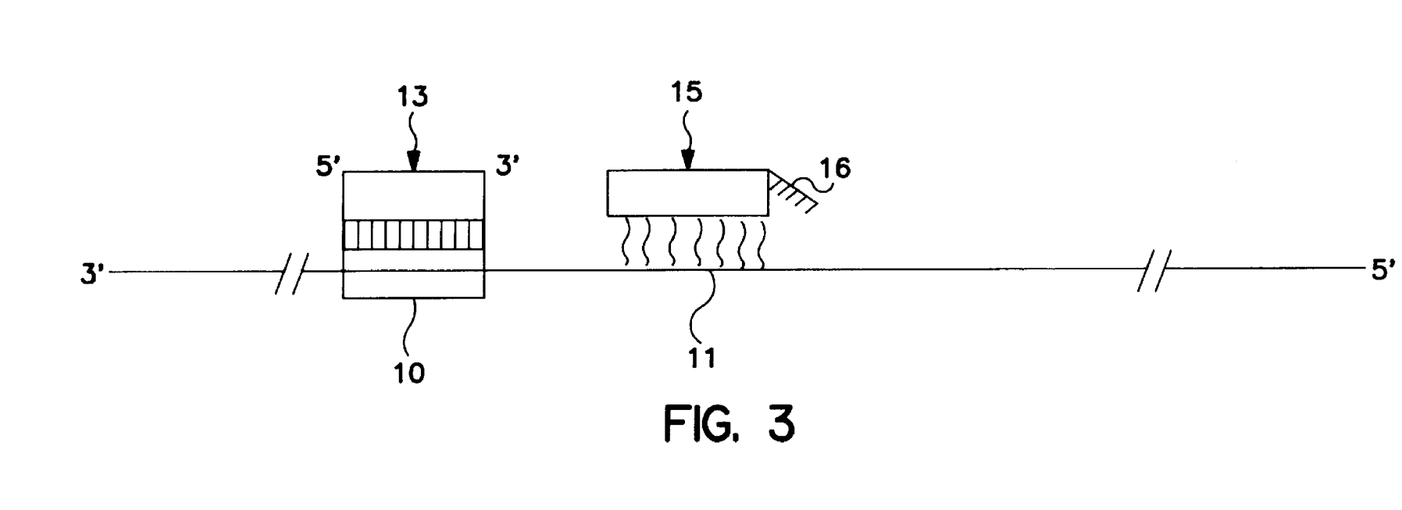
FIG. 3 schematically shows a partially single stranded DNA template having a first primer region, a region complementary to the second primer region and an inter-primer region with the first primer and blocker attached to their complementary regions.

FIG. 3 shows the nucleic acid sequence of FIG. 1 having primer attachment region (10) with the inter-primer region (11) adjacent to its 3'-end and extending to the region that is complementary to the second primer region. The region following the interprimer region (11) is complementary to the second primer region (12) which is the attachment region for the second primer (14). FIG. 3 also shows the binding of primer (13) to the first primer region (10) and the binding of non-extendable oligonucleotide blocker (15) to a sequence within the inter-primer region 11. Such binding takes place by the formation of hydrogen bonds between complementary bases in the anti-parallel nucleic acid strands. Thus, only such sequences with an adequate length of complementarity will form bonds whose collective strength is sufficient to result in stable binding.

When the blocker (15) is attached to the blocker binding region, extension from the 3' end of the first primer, through the region complementary to the inter-primer region (11) is prevented unless the blocker can be removed. When the polymerase used is Taq polymerase, that enzyme also has an enzymatic activity (a 5' exonuclease activity) that can remove a bound oligonucleotide blocking extension of the first primer, such as the non-extendable blocker (15). When a polymerase is used that lacks that activity (such as the Stoffel fragment of Taq polymerase), the blocker cannot be efficiently removed and extension from the first primer is prevented beyond the region where the blocker is bound. As an alternative to using a polymerase lacking 5'-exonuclease activity, a blocker could be used that is made resistant to the action of such exonucleolytic activity. For example, one such blocking oligonucleotide can be easily synthesized by replacing the first (5'-most) phosphodiester bond with a thioester bond that resists exonucleolytic cleavage. Other, analogous strategies might also be used to prevent exonucleolytic removal of the blocking oligonucleotide. (It should be noted that although some polymerases may have a strand displacement activity that could, in principle, remove such a blocking oligonucleotide without having to digest it exonucleolytically, this displacement activity is insufficient to allow effective amplification under the conditions described.) Since the blocker is not extendable, it cannot itself act as a primer and be extended. Therefore no extension from the first primer or from the blocker to the region complementary to the second primer can take place and amplification of that template is inhibited. This will occur only when a blocker is present that can bind to the inter-primer region of the template as shown. Therefore, the inhibition of amplification in the presence of a blocker with a specific sequence implies that the blocker had bound to a sequence in the inter-primer region of the template. If a template was used that possessed the same first and second primer regions but lacked the region complementary to the blocker, then amplification could take place even in the presence of the blocker. Thus the blocker allows one to distinguish between two templates with the same primer regions but that differ in their inter-primer regions in this way. It also can allow selective inhibition of amplification of one or more such templates (all possessing substantially the same primer regions) in the same reaction mixture, while allowing amplification to proceed uninhibited from other templates, depending on the presence or absence of inter-primer sequences complementary to those of the blocker.

Amplification is typically carried out by cycling the temperature of the reaction mixture in a device known as a thermocycler. When the first primer (13), second primer (14) and the non-extendable oligonucleotide blocker (15) are mixed with a DNA polymerase lacking 5' exonuclease activity, such as the Stoffel fragment of Taq polymerase, and with a DNA sequence having the DNA template (2), along with the necessary precursor molecules and the appropriate buffer, and the mixture is subjected to a PCR thermocycle, the non-extendable oligonucleotide blocker (15) binds to its complementary inter-primer region (11), as shown in FIG. 3. However, it is noted that a non-thermocycling procedure can potentially be used instead of the multiple temperature PCR thermocycle described above since the present method would apply to any primer-extension-dependent means of DNA amplification. Also, it is noted that the first primer region and second primer region are symmetrical as is the amplification reaction. Therefore, a blocker could also inhibit amplification by preventing extension of the second primer in exactly the same manner as described for the first primer. It is therefore arbitrary that the method is described with respect to the first primer as it could equally well have been described with respect to the second primer.

In a preferred embodiment of the invention, the non-extendable oligonucleotide blocker has a higher melting point (e.g., by at least about 5° C.) than the melting point of the first and second primers. The PCR admixture containing the higher melting point blocker is subjected to at least one thermocycle that includes an incubation step during the early part of hybridization at a temperature above that at which the first primer anneals, but below the melting point of the non-extendable oligonucleotide blocker. This assures that annealing of the non-extendable oligonucleotide blocker to the inter-primer region is favored over annealing of the first primer to its complementary region and therefore before it can be extended.

Another method of assuring that the blocker anneals to the inter-primer region before the primers anneals to its complementary region, is achieved by adding a molar excess of the blocker, over the concentration of the first primer, to the PCR admixture. These are just examples of methods which can be employed to favor blocker annealing over primer extension, thereby inhibiting amplification, and the present invention is not limited to these methods.

Also, it is possible that under some circumstances it will be unnecessary for the blocker to have any kinetic advantage over the primer in binding but can significantly block its extension and hence amplification as described without such an advantage. Therefore, the present invention is not limited to those blockers that do possess such a kinetic advantage.

After the admixture is subjected to the thermocycles of the PCR, conventional methods may be employed to detect whether amplification has been inhibited.

Electrophoresis and staining can be used to detect the presence or absence of the inhibited target DNA. Other conventional means can also be used to detect the presence or absence of the amplified nucleic acid sequence, including but not limited to, detection by Southern blotting, dye indicators and the use of spectrometers.

The method of the present invention may be adapted to detect the presence of pathogenic bacteria. For this purpose, a kit may be employed. The kit contains the following components: a PCR buffer, at least first and second oligonucleotide primers which are complementary to the first and second separated regions on a nucleic acid template, a non-extendable oligonucleotide blocker complementary to at least a portion of an inter-primer region on the nucleic acid template, and a polymerase lacking 5' exonuclease activity. Typically, such a kit would also contain a third and fourth primer, targeting a region of the template remote from the region targeted by the first and second primers and thus carrying a different inter-primer region that is not complementary to the blockers. These last two primers can act as internal positive controls to assure that nonspecific inhibition of amplification had not taken place.

For example, a kit may include a single pair of primers which is capable of binding to first and second primer regions common to a number of different bacteria. Such regions are found in the DNA sequences coding for the small ribosomal subunits, for example. In particular, the kit may include a single pair of primers capable of amplifying a homologous 240 bp region of *E. coli, S. aureus* and *N. gonorrhoea*. In addition to the primers, a non-extendable "Iblocking" oligonucleotides with sequences complementary to the inter-primer regions of the bacteria are included.

The kit may be used to identify which of these three pathogenic organisms is present in a sample. For example, a sample containing nucleic acids sequences may be added to the admixture. The admixture is then subjected to multiple PCR thermocycles. If the specific inter-primer region complementary to one of the blockers is present in the sample, then the complementary non-extendable blocker will bind to that region. Since the Stoffel fragment of Taq polymerase is included in the kit, the blocker will not be digested. Since the blocker cannot be removed in this way, the first primer cannot be extended to meet the region complementary to the second primer and that target DNA will not be amplified. If a third and fourth primer are included, as described above, targeting a region common to all 3 bacterial DNA's that differs in length from the region targeted by primers one and two, then, even where primers one and two are inhibited by the blocker, amplification by primers 3 and 4 will still take place and its product can be detected. Other methods could also be used to be certain that the blocking was specific and the invention is not confined to this method. Typically an additional reaction will be performed omitting that specific blocker. In this way the absence of amplification of the region targeted by primers 1 and 2 could be shown to be due to specific blocking and not to the absence of that DNA from the reactions.

When the PCR thermocycles are completed, the DNA is separated by length using agarose gel electrophoresis (minigel) and, after staining with ethidium bromide, is visualized under ultraviolet light. Since the amplification product of primers 3 and 4 is different in length from that resulting from primers 1 and 2, the absence of the product of primer 1 and primer 2 in the presence of the products of primer 3 and primer 4 would be apparent on the gel and allow the conclusion that amplification of the target defined by primer 1 and primer 2 had been blocked specifically by the blocker. (Assuming that the product of primer 1 and primer 2 was detected in a parallel control reaction lacking that specific blocker.) It could be further inferred that the bacterial DNA in the reaction mixture was derived from the bacterium whose inter-primer region was complementary to the blocker and not to one of the other 2 bacterial species. Conversely, if amplification was not inhibited, the bacterial DNA must have come from one of the species whose inter-primer region was not complementary to the blocker.

Figure 4:
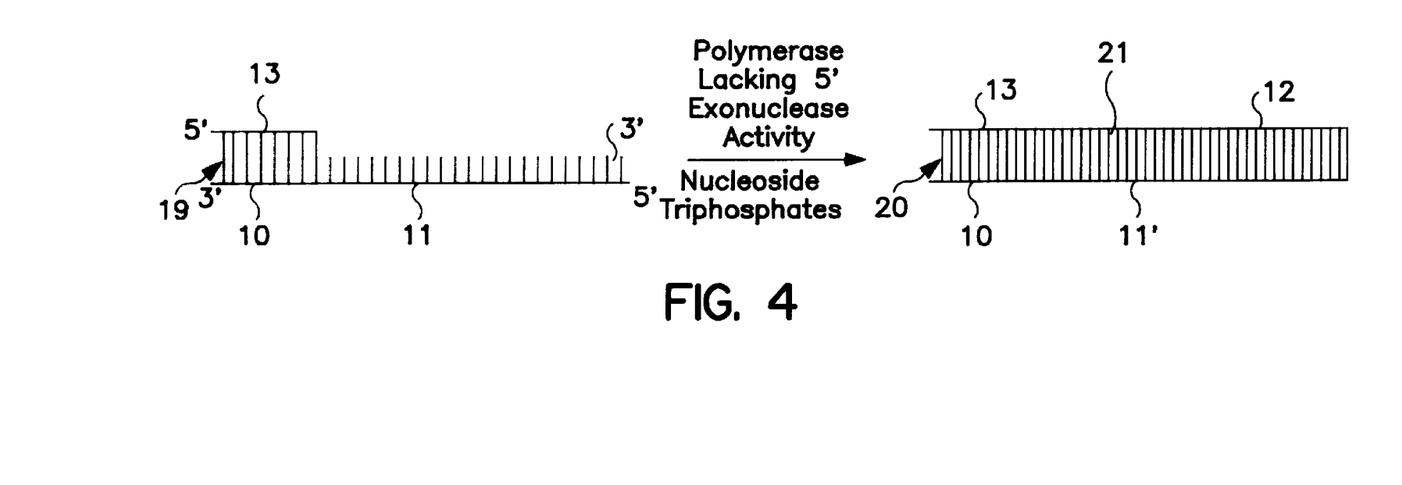
FIG. 4 schematically shows the synthesis of an extension product by using a polymerase lacking 5' exonuclease activity, where the blocker is unable to bind to an inter-primer region of a DNA template.

FIG. 4 shows a nucleic acid sequence having primer attachment region (10) with inter-primer region (11) adjacent to its 3' end and extending to the region that is complementary to the second primer region. When polymerase lacking 5' exonuclease activity is added to the nucleic sequence together with nucleotide triphosphates, primer (13) will bind to its complementary region (10) and extension of the primer will occur as shown. This is the process that occurs in the absence of a non-extendable blocker.

The method of the present invention may also be adapted for use in genetic research. For this purpose, for example, the kit can be made to include primers targeting a gene with two allotypes, one of which contains an insertion relative to the other, such that a blocker can be synthesized to bind to that insertion and therefore block amplification only of the allotype that carried the insertion. Unblocked amplification would then reveal the presence of the allotype lacking the insertion, even if the other allotype were also present. If the length of the insertion were relatively short, the products from the amplification of the two alleles could not easily be distinguished by length alone using electrophoresis, but could still be so distinguished by their differential amplification in this way.

More generally, the method of the present invention may also be adapted for use in any situation where it is desired to amplify one target (or group of targets) in the presence of another target (or group of targets) whose amplification one does not desire but which is potentially amplifiable because it possess sequences in common with the first target that will allow it to be amplified by the same two primers. Such situations might occur whenever primers are used that target multiple sequences. One example of where that occurs is with representational difference analysis, during the course of which artificial oligonucleotide sequences are introduced at the ends of multiple target sequences and then amplified with a common pair of primers. Another such situation might arise where primers targeting multiple bacterial DNA's are used but where a known amplifiable DNA contaminant is present whose amplification could obscure the presence of other targets. Such a contaminating bacterial DNA is commonly present in most preparations of Taq polymerase, for example. Still another such situation might occur where 2 differently spliced mRNA's might result from transcription of the same gene through alternate slicing, but where a single pair of primers could target both cDNA's. If the shorter message were present in small amounts relative to that of the longer message, its cDNA amplification might be obscured or inhibited by the amplification of the dominant target. If the latter could be inhibited by a blocker targeting a region absent in the shorter message, it could allow amplification of the cDNA of the latter to result and its presence thus revealed. Other similar applications can readily be devised by those skilled in the art and considered to be within the scope of the invention.

In order that the invention described herein may be more fully understood, the following examples are set forth. It should be understood that the following examples are for illustrative purposes only and are not to be construed as limiting the invention.

EXAMPLE 1

Experiments were conducted to determine if the inhibition of amplification could be detected for a target DNA. The DNA used in this example was obtained either commercially from Sigma Chemical Co., St. Louis, Mo., or prepared by routine phenol-chloroform extraction from strains obtained from the American Type Culture Collection, Rockville, Md. Oligonucleotides were synthesized by Operon Technologies, Alameda, Calif. The sequences and specificities of the oligonucleotides employed in this example are summarized in Table 1 below. Sequence information was obtained from published databases (Nucleic Acids Research 21 (Supplement): 3021–3023).

Targets were chosen from the partially conserved ribosomal 16S DNA of three species of bacteria: *E. coli, B. subtilis,* and *N. gonorrhoea* as shown in Table 1. A single pair of primers is capable of amplifying a homologous 240 bp region of all three. Two non-extendable "blocking" nucleotides were synthesized with the sequences complementary to the inter-primer regions of *E. coli* and *B. subtilis*, respectively also shown in Table 1.

A PCR reaction mixture was prepared as follows, all amounts being given for a 100 μl final reaction volume although in some experiments half that volume was actually used. Each PCR mixture contained 10 mM Tris pH 8.3, 10 mM KCl, 3 mM $MgCl_2$, 200 uM each of the four deoxynucleotide triphosphates (Pharmacia, Piscataway, N.J.), 5 units of Taq polymerase (Perkin Elmer, Norwalk, Conn.), or of the Stoffel fragment, (also available from Perkin Elmer), 100 pg of bacterial DNA and 2.5 pm of primers p1 and p2 and 50 pm of primers p3 and p4. Blocking oligonucleotides, where used, were at 20 pm for BE and BB at 250 pm for the others.

After covering with mineral oil the reaction mixture was subjected to the indicated number of thermal cycles (Perkin Elmer Thermocycler, model 4810), using the hot start method (Nucleic Acids Res. 20: 1717–1723). Each cycle consisted of 1 min at 94° C., 20 sec at 63° C. and 10 sec at 52° C., with an initial heating at 94° C. for 4 min and, following completion of cycling, at 52° C. for 4 min. Ten ul aliquots of PCR products along with appropriate DNA size standards were subjected to electrophoresis on 1.5% agarose gel, stained with ethidium bromide and photographed under UV illumination.

Southern blotting employed nylon membranes (Zeta-probe, Biorad, Richmond, Va.). Southern transfers, 5'-end radiolabelling of the probe, hybridization and autoradiography as standard in the field were used. All standard precautions were employed to minimize the risk of contamination, including the use of cotton plugged pipettes.

Figure 5:
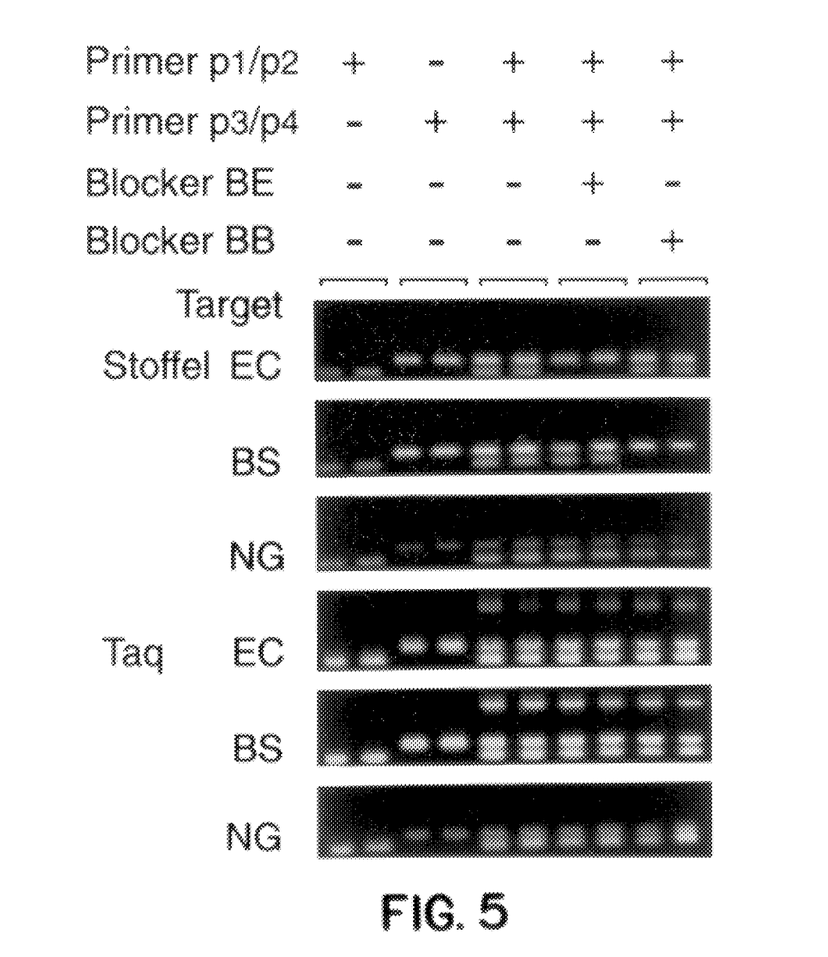
FIG. 5 shows the results of Example 1 as photographs of UV-illuminated, ethidium bromide-stained gels, each photograph showing a set of five reactions, each in duplicate.
Figure 6:
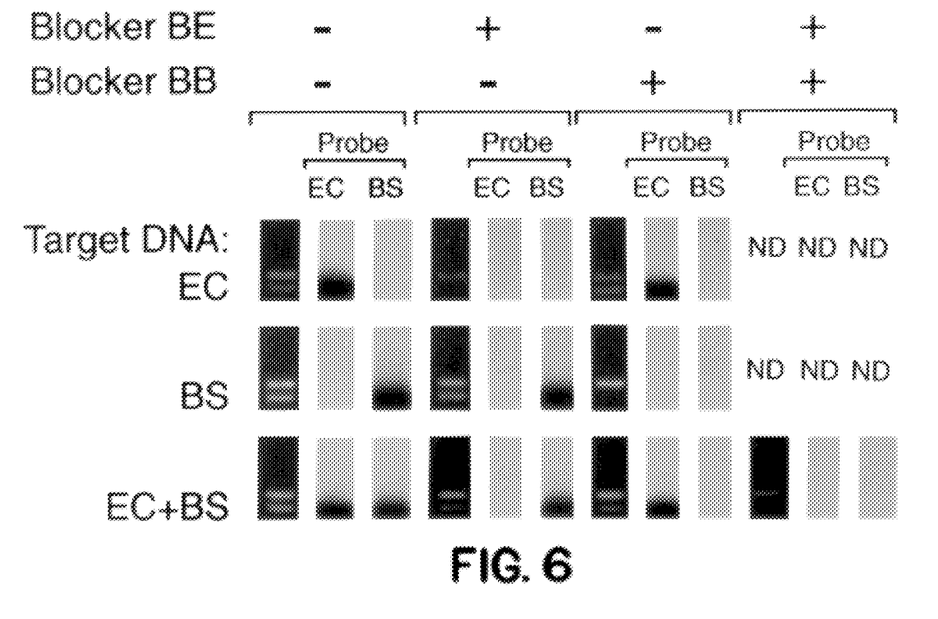
FIG. 6 shows the results of Example 1 as Southern blots and ethidium bromide-stained gels applied to a mixture of bacterial DNA and allowing one to distinguish each target.

The results obtained are shown in FIGS. 5 and 6.

In FIG. 5, blockers BB and BE were shown to specifically prevent amplification of DNA from *B. subtilis* (BS) and *E. coli* (EC) respectively, but not from *N, gonorrhoea* (NG), Blocker BA, whose sequence is similar to that of blocker BB, behaved in the same manner as did blocker BB. A positive internal control is provided by the inclusion of primers p3 and p4 that target a sequence, present in all 3 DNA's, but whose inter-primer region is not targeted by any of the blockers and which is therefore not inhibited by any of the blockers. The region targeted by p3 and p4 is longer

TABLE 1

Oligonucleotides used (all shown 5' to 3').

| Oligonucleotide | E. coli | B. subtilis | S. aureus | N. gonorrhoea | Sequence | Location* |
|---|---|---|---|---|---|---|
| P1 | + | + | + | + | GGAGGAAGGTGGGGATGAC (SEQ ID NO: 1) | 1174–1192 |
| P2‡‡ | + | + | + | + | TACACACCGCCCGTCACACCA (SEQ ID NO: 2) | 1393–1413 |
| P3 | + | + | + | + | GATTAGATACCCTNGTAG § (SEQ ID NO: 3) | 786–803 |
| P4‡‡ | + | + | + | + | TAAGTCCCGCAACGAGCGCA (SEQ ID NO: 4) | 1091–1110 |
| BE | + | − | − | − | CGCATACAAAGAGAAGCGACCTCGCGAGAGCAAGCG GACCTatcg ¶ (SEQ ID NO: 5) | 1243–1287 |
| BB | − | + | +† | − | ACAGAACAAAGGGCAGCGAAACCGCGAGGTTAAGCC AATCCatgc (SEQ ID NO: 6) | 1243–1287 |
| BA | − | +† | + | − | ACAATACAAAGGGCAGCGAAACCGCGAGGTCAAGCA AATCCatgc (SEQ ID NO: 7) | 1243–1287 |

*in *E. coli*.
‡"+" indicates a complementary sequence; "−" indicates noncomplementary.
†indicates close but imperfect homology.
‡‡antisense primers shown as reversed complements.
§ "N" indicates deoxyinosine.
¶ Lower case bases indicate noncomplementary 3' termini of blocking oligonucleotides.

than that targeted by primers p1 and p2 and therefore runs more slowly (seen as the higher of the two bands) on electrophoresis. When Taq polymerase is substituted for the Stoffel fragment in the reaction mixture, no inhibition of amplification takes place so that both the p1/p2 and p3/p4 bands appear in all reactions. (In the bottom reaction, a third (slower) band appears, probably due to a "read-through" product from the 5'most primer to the 3'-most primer).

In FIG. 6 is shown the application of the blocking method to mixed targets with characterization of the products on Southern blots. On each of the 3 rows is shown an experiment with a different target. The first row contains EC as target, the second, BS and the third, an equal mixture of EC and BS DNA. Each reaction was subjected to 25 cycles and contained the Stoffel fragment as well as all 4 primers, p1, p2, p3 and p4. Thus, both the slower p3/p4 internal control product and the faster p1/p2 experimental product are visible in the unblocked reactions (shown at the left). As indicated at the top, each target was amplified in the presence of either no blocker, the BE blocker, the BB blocker or both BE and BB blockers (only applied to the mixed targets at the bottom), shown from left to right as indicated. Each reaction was analyzed in 3 ways, shown from left to right, by EB-staining of the gel, and by autoradiographs of Southern blots, that had been probed with a radiolabeled oligonucleotide complementary to either EC or BS as shown. In each case the probe detected the unblocked PCR product(s), but not the blocked product or the control amplicon. The mobilities of the bands seen on the stained gels are the same as on the corresponding gels in FIG. 5. Of interest is the result with the mixed targets where, although the stained gel fails to distinguish between the products derived from the 2 targets, the probes demonstrate differential blocking as expected. Moreover, when both blockers are used, both products are eliminated, both on the gel and on the autoradiographs.

EXAMPLE 2

Figure 7:
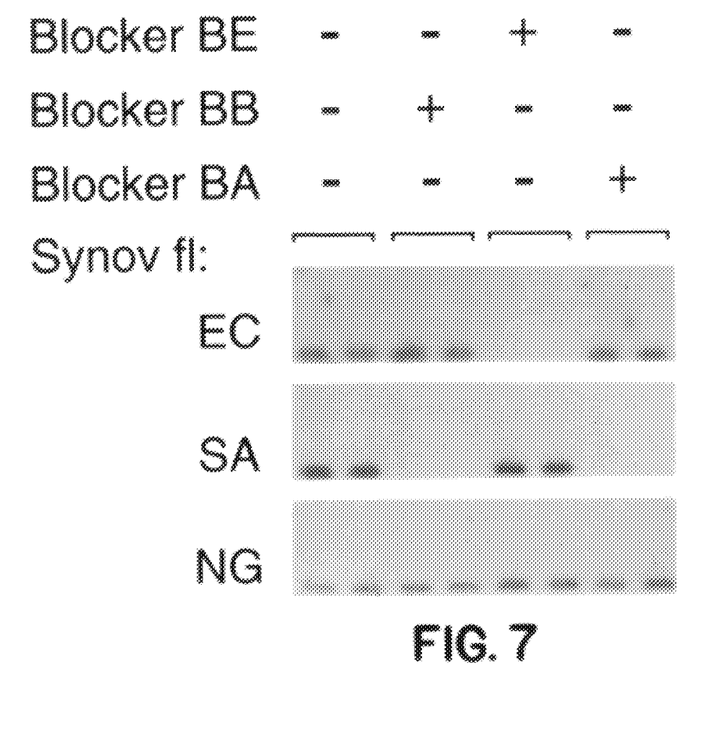
FIG. 7 shows the results of Example 2 as a Southern blot of a PCR admixture using primers p1 and p2 to amplify extracts from synovial fluid specimens infected, from top to bottom, with *E. coli*, *S. Aureus*, and *N. gonorrhoea*.

In another experiment, the sequence dependent inhibition of PCR-based amplification was used to distinguish among three different bacterial infections present in human joint fluid. FIG. 7 depicts a Southern Blot reporting the results of the experiment using a PCR admixture containing different blockers that are complementary to the inter-primer regions located on E. coli and S. Aureus (SA). Table 1 shows the sequences of the primers, blockers, and their respective locations. The PCR mixture was made and the PCR thermocycle was performed as in Example 1, but with a simple DNA extract clinically infected joint fluid specimen where the infecting organisms have already been detected by routine methods.

As shown in FIG. 7 at the line labelled EC, where DNA extracts from joint fluid from a patient infected with E. coli were present in the PCR mixtures, sequence dependent inhibition of amplification occurred in experiment three (Column 3) where the E. coli blocker (BE) is present. In the other experiments where the E. coli blocker is not present, normal amplification is observed. This indicates that the E. coli blocker (BE) can be used to distinguish infection with E coli, from that with either N. gonorrhoea or S. aureus (SA).

As apparent at the line labelled SA in FIG. 7, sequence dependent inhibition of amplification has occurred in experiments 2 and 4 (Columns 2 and 4 respectively), containing blockers BB and BA which contain almost the same sequences and which therefore behave identically here. The other reactions are not inhibited indicating again that sequence dependent inhibition of amplification occurred. This indicates that the BB/BA blocker can be used to distinguish infection with S. aureus from infection with either E. coli or with N. gonorrhoea.

Blockers for N. gonorrhoea are not present in any of the experiments depicted. The row labeled NG, containing DNA extracted from specimens infected with N. gonorrhoea, shows no inhibition with any of the blockers. Thus, no sequence dependent inhibition of amplification resulted. This further demonstrates the specificity of the blockers used in the experiments and their ability to distinguish among infections with these organisms.

While the invention has been described by reference to specific embodiments, this was for purposes of illustration only. Numerous alternative embodiments will be apparent to those skilled in the art and considered to be within the scope of the invention.

---

I claim:

1. A method of specific inhibition of amplification of at least one target sequence located on at least one DNA sequence in the polymerase chain reaction (PCR), comprising:

forming a PCR admixture comprising at least one DNA target sequence, at least first and second oligonucleotide primers which are complementary to first and second separated regions on said target sequence, at least one non-extendable oligonucleotide blocker complementary to at least a portion of an inter-primer region located between said first primer region and the sequence complementary to said second primer region on said target sequence, said oligonucleotide blocker comprising a plurality of nucleotides connected to each other by phosphodiester linkages, appropriate buffers and nucleic acid precursors, and a nucleic acid polymerase which lacks 5' exonuclease activity; and subjecting said PCR admixture to at least one PCR thermocycle comprising hybridization, primer extension and denaturation, whereby amplification of said target sequence is inhibited when said at least one non-extendable oligonucleotide blocker anneals to said at least one inter-primer regions of said target sequence.

2. The method of claim 1 wherein said non-extendable oligonucleotide blocker has at least one 3' mismatch relative to said target sequence.

3. The method of claim 1 wherein said nucleic acid polymerase is the Stoffel fragment of Taq polymerase.

4. The method of claim 1 wherein said non-extendable oligonucleotide blocker has a higher melting point than the melting point of said first primer.

5. The method of claim 4 wherein said PCR thermocycle includes an incubation step at a temperature higher than the annealing point of said first primer and lower than the annealing point of said non-extendable oligonucleotide blocker.

6. The method of claim 5 wherein said PCR admixture includes a molar excess of said non-extendable oligonucleotide blocker over said first and second primers.

7. The method of claim 1 further comprising detecting amplification of said target sequence.

8. The method of claim 1 wherein said non-extendable oligonucleotide blocker terminates at its 5' end in a 2',3'-dideoxynucleotide.

9. A method of detecting the presence of at least one specific DNA target sequence located on at least one DNA sequence in the polymerase chain reaction (PCR), comprising:

forming a PCR admixture comprising at least first and second oligonucleotide primers which are complementary to first and second separated regions on said target sequence, at least one non-extendable oligonucleotide blocker complementary to at least a portion of at least one inter-primer region located between said first primer region and a sequence complementary to said second oligonucleotide primer on said target sequence, said oligonucleotide blocker comprising a plurality of nucleotides connected to each other by phosphodiester linkages, appropriate buffers and nucleic acid precursors, and a DNA polymerase which lacks 5' exonuclease activity;

adding an unknown sample to be tested for the presence of said target to said PCR admixture;

subjecting said PCR admixture including said unknown sample to at least one PCR thermocycle comprising hybridization, primer extension and denaturation, wherein amplification will be inhibited during said PCR thermocycle when said non-extendable oligonucleotide blocker anneals to said at least one inter-primer of said target sequence; and detecting whether amplification of said target sequence has been inhibited by comparing said PCR admixture including said unknown sample with a parallel reaction in which said non-extendable oligonucleotide blocker is omitted, wherein the absence of amplification of said target sequence in said PCR admixture containing said unknown sample together with amplification of said target in said parallel reaction indicates the presence of said target sequence in said PCR admixture comprising said unknown sample.

10. The method of claim 9 wherein said DNA polymerase is the Stoffel fragment of Taq polymerase.

11. The method of claim 9 wherein said PCR thermocycle includes an incubation step at a temperature higher than the annealing point of said first primer and lower than the annealing point of said non-extendable oligonucleotide blocker.

12. The method of claim 9 wherein said first and second primers are complementary to first and second primer regions present on nucleic acid of *E. coli*, *S. aureus*, or *N. gonorrhoea*; and said non-extendable oligonucleotide blocker is complementary to at least a portion of the inter-primer region present on the nucleic acid of *E. coli*, *S. aureus*, or *N. gonorrhoea*.

13. The method of claim 9 wherein said PCR thermocycle includes a hybridization step at a temperature in the range of 50° to 80° C., a primer extension step at a temperature in the range of about 50°–80° C., and a denaturation step at a temperature in the range of about 90° to 100° C.

14. The method of claim 9 wherein said PCR thermocycle is begun at a temperature of about 85° to 100° C.

15. The method of claim 9 wherein said PCR admixture includes a molar excess of said non-extendable oligonucleotide blocker relative to said first primer.

16. The method of claim 9 wherein said non-extendable oligonucleotide blocker has at least one 3' mismatch relative to said target sequence.

17. The method of claim 9 wherein said non-extendable oligonucleotide blocker terminates at its 5' end in a 2',3'-dideoxynucleotide.

18. A kit for detecting the presence of a specific nucleic acid sequence in a sample, comprising:

a PCR admixture comprising at least first and second oligonucleotide primers which are complementary to first and second separated regions on said specific nucleic acid sequence, at least one non-extendable oligonucleotide blocker complementary to at least a portion of an inter-primer region between said first primer region and said region complementary to said second primer region on said specific nucleic acid sequence, said oligonucleotide blocker comprising a plurality of nucleotides connected to each other by phosphodiester linkages, and a polymerase lacking 5' exonuclease activity.

19. The kit of claim 18 further comprising electrophoresis reagents.

20. The kit of claim 18 further comprising a second pair of primers, primer 3 and primer 4, targeting a region different from that targeted by primers 1 and 2 and that includes an inter-primer region to which said non-extendable oligonucleotide blocker does not bind and whose amplification would therefore not be inhibited by said non-extendable oligonucleotide blocker, in order to control for nonspecific inhibition of amplification.

21. The kit of claim 18 wherein said first and second primers that are complementary to separated regions on nucleic acid of *E. coli, S. aureus,* or *N. gonorrhoea*; and non-extendable oligonucleotide blockers that are complementary to at least a portion of the inter-primer regions of nucleic acid of *E. coli, S. aureus,* and *N. gonorrhoea.*

22. The kit of claim 18 wherein said polymerase is the Stoffel fragment of Taq polymerase.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 19 base pairs
        ( B ) TYPE: Nucleic Acid
        ( C ) STRANDEDNESS: Single stranded
        ( D ) TOPOLOGY: Linear     ( i i ) MOLECULE TYPE: Genomic DNA     ( x i ) SEQUENCE DESCRIPTION: SEQ ID NO: 1:

GGAGGAAGGT GGGGATGAC ( 2 ) INFORMATION FOR SEQ ID NO: 2:

( i ) SEQUENCE CHARACTERISTICS:
        ( A ) LENGTH: 21 base pairs (B) TYPE: Nucleic Acids
(C) STRANDEDNESS: Single stranded
(D) TOPOLOGY: Linear (ii) MOLECULE TYPE: Genomic DNA (xi) SEQUENCE DESCRIPTION: SEQ ID NO: 2:

TACACACCGC CCGTCACACC A    21

(2) INFORMATION FOR SEQ ID NO: 3:

(i) SEQUENCE CHARACTERISTICS:
(A) LENGTH: 18 base pairs
(B) TYPE: Nucleic Acids
(C) STRANDEDNESS: Single stranded
(D) TOPOLOGY: Linear (ii) MOLECULE TYPE: Genomic DNA (ix) FEATURE:
(D) OTHER INFORMATION: N =DEOXYINOSINE (xi) SEQUENCE DESCRIPTION: SEQ ID NO: 3:

GATTAGATAC CCTNGTAG    18

(2) INFORMATION FOR SEQ ID NO: 4:

(i) SEQUENCE CHARACTERISTICS:
(A) LENGTH: 20 base pairs
(B) TYPE: Nucleic Acids
(C) STRANDEDNESS: Single stranded
(D) TOPOLOGY: Linear (ii) MOLECULE TYPE: Genomic DNA (xi) SEQUENCE DESCRIPTION: SEQ ID NO: 4:

TAAGTCCCGC AACGAGCGCA    20

(2) INFORMATION FOR SEQ ID NO: 5:

(i) SEQUENCE CHARACTERISTICS:
(A) LENGTH: 45 base pairs
(B) TYPE: Nucleic Acids
(C) STRANDEDNESS: Single stranded
(D) TOPOLOGY: Linear (ii) MOLECULE TYPE: Genomic DNA (xi) SEQUENCE DESCRIPTION: SEQ ID NO: 5:

CGCATACAAA GAGAAGCGAC CTCGCGAGAG CAAGCGGACC TATGC    45

(2) INFORMATION FOR SEQ ID NO: 6:

(i) SEQUENCE CHARACTERISTICS:
(A) LENGTH: 45 base pairs
(B) TYPE: Nucleic Acids
(C) STRANDEDNESS: Single Stranded
(D) TOPOLOGY: Linear (ii) MOLECULE TYPE: Genomic DNA (xi) SEQUENCE DESCRIPTION: SEQ ID NO: 6:

ACAGAACAAA GGGCAGCGAA ACCGCGAGGT TAAGCCAATC CATGC    45

(2) INFORMATION FOR SEQ ID NO: 7:

(i) SEQUENCE CHARACTERISTICS:
(A) LENGTH: 45 base pairs
(B) TYPE: Nucleic Acids
(C) STRANDEDNESS: Single Stranded -continued ( D ) TOPOLOGY: Linear ( i i ) MOLECULE TYPE: Genomic DNA ( x i ) SEQUENCE DESCRIPTION: SEQ ID NO: 7:

ACAATACAAA GGGCAGCGAA ACCGCGAGGT CAAGCAAATC CATGC    4 5